United States Patent
Bartoleyns et al.

(10) Patent No.: US 6,616,925 B1
(45) Date of Patent: *Sep. 9, 2003

(54) COMBINED PREPARATION FOR THE TREATMENT OF NEOPLASIC DISEASES OR OF INFECTIOUS DISEASES

(75) Inventors: Jacques Bartholeyns, Bures-sur-Yvette (FR); Yves Fouron, Marlborough, MA (US); Jean-Loup Romet-Lemonne, Paris (FR)

(73) Assignee: I.D.M. Immuno-Designed Molecules, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/081,443

(22) Filed: May 19, 1998

(30) Foreign Application Priority Data

Apr. 2, 1998 (EP) .............................................. 98400783

(51) Int. Cl.$^7$ .......................... A01N 63/00; A01N 37/18; C12N 5/00; C12N 5/06; A61K 48/00; A61K 38/00
(52) U.S. Cl. .................. 424/93.7; 424/93.1; 424/93.21; 424/93.71; 435/325; 435/363; 435/366; 435/372; 435/372.1; 435/375; 435/383; 514/2
(58) Field of Search .............................. 424/93.1, 93.21, 424/93.7, 93.71; 514/2; 435/375, 325, 363, 366, 372, 383, 372.1

(56) References Cited

PUBLICATIONS

Sukh Mahendra et al, Interaction between Cisplatin–Treated Macrophages and Dalton's Lymphoma Cells In Vito, Expl Cell Biol. 56:1–11 1988.*
Van Schie et al. In vitro studies on the influence of doxorubicin in combination with recombinant interferon –gamma on human monocytes. AntiCancer Research. vol. 11, pp. 1245–1252. 1991.*
Takeda et al. The effect of local immunotherapy for breast cancer using a mixture of OK–432 and fibrinogen supplemented with activated macrophages. Biotherapy. vol. 7, 47–54, 1994.*
Bartoleyns et al. Immune therapy with macrophages: present status and critical requirements for implementation. Immunobiology. vol. 195, pp. 550–562, 1996.*
Andreesen R., et al A new approach to adoptive immunotherapy of cancer using tumorcytotoxic macrophages grown from peripheral blood monocytes, Cancer Detect Prev. 1991;15(5):413–21.*
Chokri M et al. Production of human macrophages with potent antitumor properties (MAK) by culture of monocytes in the presence of GM–CSF and 1,250–dihydroxy vitamin D3. Anticancer Res. Nov.–Dec. 1992, 12(6B):2257–60.*
Ogura T. Bases on timing of combined modality of chemotherapy and immunotherapy Gan To Kagaku Ryoho. Aug. 1990;17(8 Pt 1):1414–20.*
Hennemann, B, et al., "Monocyte/macrophage activation by immunostimulators: Role in cancer therapy", *Clinical Immunotherapeutics*, (Apr. 5, 1996), pp. 294–308.
Hennemann, B. et al., "Adoptive immunotherapy with tumor–cytotoxic macrophages derived from recombinant human granulocyte–macrophage colony–stimulating factor (rhuGM–CSF) mobilized peripheral blood monocytes", *Journal of Immunotherapy*, Sep. 20, 1997, pp. 365–371.
Bartoleyns, J. et al., "Immune therapy with macrophages: present status and critical requirements for implementation", *Immunobiology*, Oct. 1996, pp. 550–562.
Takeda et al., "The effect of local immunotherapy for breat cancer using a mixture of OK–432 and fibrinogen supplemented with activated macrophages", *Biotherapy*, 1994, pp. 47–54.

* cited by examiner

Primary Examiner—Jeffrey Fredman
Assistant Examiner—Sumesh Kaushal
(74) Attorney, Agent, or Firm—Young & Thompson

(57) ABSTRACT

The present invention relates to combined preparation containing as active substance the following individual components, in the form of a kit-of-parts:

monocyte derived cells, particularly cytotoxic macrophages,
  chemotherapy or immunotherapy drugs,
  for the simultaneous, separate or sequential use, for the treatment of cancer or infectious diseases.

14 Claims, 1 Drawing Sheet

COMBINED PREPARATION FOR THE TREATMENT OF NEOPLASIC DISEASES OR OF INFECTIOUS DISEASES

BACKGROUND OF INVENTION

1. Field of the Invention

The present invention relates to a new combined preparation for the treatment of neoplasic diseases or of infectious diseases.

The present invention describes sequences of conventional treatments of cancer or infections and of immunotherapies reversing or preventing chemoresistance and allowing long lasting therapeutic responses.

2. Description of the Related Art

In conventional therapy, residual tumor cells or infectious agents are left undamaged due to chemoresistance or due to the fact that these cells are shaded in protected areas or located in hypoxic areas poorly vascularized and not accessible to conventional treatments. The genetic instability and heterogeneity of tumors and micro-organisms indeed allow them to adapt and to develop resistance to therapies.

The beneficial effects of chemotherapy can be compromised by cellular mechanisms that allow infectious agents or neoplasic tissue to evade the toxicity of drugs. In some cases, pleiotropic resistance to a variety of unrelated drugs has been observed, and this phenomenon has been called multidrug resistance.

Resistance to chemotherapy, whether it is intrinsic or acquired, is a major cause of failure in the curative treatment of chronic infections or neoplasic malignancies. Among the most active anti-cancer agents used in the treatment of haematological malignancies are some natural toxin-derived drugs, such as the anthracycline daunorubicin or adriamicin, the epipodophyllotoxins, taxoter derivatives, the vinca alkaloid vincristine, cisplatin, fluorouracils.

Development of cross-resistance to these structurally and functionally unrelated drugs, called multidrug resistance, is frequently observed in second or third intention cytotoxic treatment of cancer.

Multiple drug resistance of infectious agents and particularly of bacteria to antibiotics such as penicilins, β-lactamines, cephalosporines, aminoglucosides, macrolides and sulfamides, is more and more often seen in hospitals.

Monocytes derived cells (MDCs) are immune cells such as obtained by culture of blood mononuclear cells in non adherent gas permeable plastic or Teflon bags for 5 to 10 days at 37° C. in $O_2/CO_2$ atmosphere. Their culture medium (RPMI, IMDM, AIM5 (Gibco) or X-VIVO (Biowhittaker)) contains eventually cytokines or ligands as defined in patents n° PCT/EP93/01232, n° WO94/26875 or EP 97/02703 or in the articles mentioned below:

"Autologous lymphocytes prevent the death of monocytes in culture and promote, as do GM-CSF, IL-3 and M-CSF, their differentiation into macrophages". (Lopez M., Martinache Ch., Canepa S., Chokri M., Scotto F., Bartholeyns J.; J. of Immunological Methods, 159: 29–38, 1993);

"Immnune therapy with macrophages: Present status and critical requirements for implementation" (Bartholeyns J., Romet-Lemonne J-L., Chokri M., Lopez M.; Immunobiol., 195: 550–562, 1996);

"In vitro generation of CD83+ human blood dendritic cells for active tumor immunotherapy" (Thurnher M., Papesh C., Ramoner R., Gastlt G. and al.; Experimental Hematology, 25: 232–237, 1997);

"Dendritic cells as adjuvants for immnune-mediated resistance to tumors" (Schuler G. and Steinman R. M.; J. Exp. Med., 186: 1183–1187, 1997).

All these patents applications and articles are included herein for references.

They can be activated by INF-γ at the end of culture to obtain in particular cytotoxic macrophages. They can be centrifuged to be concentrated and purified before resuspension in isotonic solution.

Monocytes derived cells (MDCs) can either be killer macrophages, phagocytozing cells, growth factors and cytokines releasing cells, or dendritic cells according to their conditions of differentiation. Dendritic cells can for example be obtained as described in "In vitro generation of CD83+ human blood dendritic cells for active tumor immunotherapy" (Thurnher M., Papesh C., Ramoner R., Gastlt G. and al.; Experimental Hematology, 25: 232–237, 1997) and "Dendritic cells as adjuvants for immune-mediated resistance to tumors" (Schuler G. and Steinman R. M.; J. Exp. Med., 186: 1183–1187, 1997), and EP n° 97/02703.

In addition, activated monocyte derived cells (macrophages) can be used to deliver therapeutic agents to tumor or infectious sites.

SUMMARY OF THE INVENTION

One of the aims of the invention is to provide a combined preparation of active substances under the form of individual components for the simultaneous separate or sequential use, in the treatment of cancer or of infectious diseases.

Another aim of the invention is to provide a method for the treatment of residual cancer resistant to chemotherapy.

Another aim of the invention is to provide a method for the treatment of infectious diseases resistant to antibiotic treatment.

The invention relates to a combined preparation containing, as active substance, the following individual components, in the form of a kit-of-parts:

monocyte derived cells, particularly cytotoxic macrophages, chemotherapy or immunotherapy drugs, for the simultaneous, separate or sequential use, for the treatment of cancer or infectious diseases.

The present treatment consists in the local or systemic injection of autologous activated macrophages (MAK® killer cells) or monocyte derived cells which have access to injured areas, and in particular to hypoxic areas, where they tend to concentrate.

This treatment can be conducted after first failure and relapse following chemotherapies, or before chemotherapy, to prevent chemoresistance. Local treatment with chemotherapy drugs causes cell necrosis and release of chemokines which call and actively recruit macrophages and monocytes derived cells. Therefore, combining the chemotherapy with macrophage immunotherapy can in synergy increase cytotoxicity and increase immune response at the same time as preventing the establishment of resistance. Additionally to a first treatment combining conventional approach with immunotherapy, macrophage adoptive therapy can be proposed after failure and relapse.

It is shown through the invention that the local or systemic injection of activated monocyte derived cells, or macrophages, restores clinical responses to cytotoxic drugs for which resistance was previously demonstrated, or prevents the apparition of chemoresistance.

The present invention also shows that activated monocyte derived cells can overcome this resistance and synergize for therapy.

The two active ingredients of the combined preparation have never been used for a new joint effect and are unknown as a composition.

The active ingredients which are administered either at the same time, or separately, or sequentially, according to the invention, do not represent a mere aggregate of known agents, but a new combination with the surprising valuable property that immunotherapy with monocyte derived cells modifies the chemoresistance/chemosensitivity and allows a new effective treatment (partial or complete response) with similar chemotherapy protocole. Furthermore, synergy is observed between monocyte derived cells immunotherapy and chemotherapy.

It is to be stressed that the combined preparation also designated by a kit-of-parts means that the components of the combined preparation are not necessarily present as a union e.g. in composition, in order to be available for separate or sequential application. Thus the expression kit-of-parts means that it is not necessarily a true combination, in view of the physical separation of the components.

In an advantageous combined preparation of the invention, the monocyte derived cells contain chemotherapy or immunotherapy drugs.

In another advantageous combined preparation of the invention, the monocyte derived cells are such as prepared according to the method comprising the following steps:

1) recovery of blood derived mononuclear cells directly from blood apheresis or from blood bag collection, followed if necessary by centrifugation, to eliminate a substantial part of red blood cells, granulocytes and platelets, and collection of peripheral blood leukocytes;

2) washing peripheral blood leukocytes obtained at the preceeding steps for instance by centrifugation (to remove 90% of platelets, red blood cells and debris) to obtain mononuclear cells;

3) resuspension of the total mononuclear cells (monocytes+lymphocytes) obtained at the preceeding step in culture medium (RPMI or IMDM type) at $10^6$ to $2.10^7$ cells/ml, possibly completed by cytokines and/or autologous serum, and culture for 5 to 10 days at 37° C. under $O^2/CO_2$ atmosphere in hydrophobic gas permeable bags, to obtain monocyte derived cells and contaminating lymphocytes.

According to an advantageous combined preparation, the chemotherapy drug is selected among cytotoxic compounds such as anthracyclins, daunorubicin, adriamycin, taxoter derivatives, vinca alcaloids, vincristine, carmustine, cisplatin, fluorouracils, cytostatic compounds such as polyamine inhibitors, topoisomerase inhibitors, tamoxifene, prodasone, or sandostatine, or compounds inducing apoptosis such as sodium butyrate or mitomycin C, antibiotics such as penicilins, β-lactamines, cephalosporines, cyclines, aminoglucosides, macrolides or sulfamides, or antiviral drugs such as AZT, protease inhibitors or acyclovir, retrovir or foscarnet.

According to an advantageous embodiment, the combined preparation of the invention is such that the immunotherapy drug is selected among cytokines such as cyclosporine, azathioprine, cyclophosphamide, IFNγ, IL-12, IL-2, GM-CSF, G-CSF, and immunoadjuvants such as murapeptides or BCG.

According to an advantageous embodiment, in the combined preparation of the invention, the monocyte derived cells and the chemotherapy or immunotherapy drugs are in the form in injectable solutions.

In another advantageous embodiment of the invention, in the combined preparation, the injectable solutions are in the form of locally injectable solutions.

In another advantageous embodiment in the combined preparation of the invention, the injectable solutions are in the form of systemically injectable solutions.

In another advantageous combined preparation of the invention, the monocyte derived cells are administered at a dose of about $10^7$ to about $10^{10}$ monocyte derived cells per injection.

In another advantageous combined preparation of the invention, the monocyte derived cells are administrated at a dose of about $10^8$ to about $10^{9.}$ In another advantageous combined preparation of the invention, the monocyte derived cells are administered in a repeated way up to ten times, the interval between each administration being between three days to two months.

In another advantageous combined preparation of the invention, the immunotherapy or chemotherapy drug is administered at a dose of about 0.1 to about 1000 mg/day.

In another advantageous combined preparation of the invention, in the case of administration of a drug chosen among immunotherapy drug, antiviral drug, cytotoxic drugs, or antibiotics, said drug is administered at a dose of about 10 to about 1000 mg/day.

More specifically, in the case of cytotoxic compounds such as vincristine, taxol, carmustine, daunorubicin, adryamicin, cisplatin, fluorouracil, they are administered at a dose of about 10 to about 500 mg/day.

In the case of antiviral drugs such as retrovir, aciclovir, foscarnet, said drug is administered at a dose of about 20 to about 500 mg/day.

In the case of antibiotics such as penicilins, cephalosporine, sulfamides, cyclines, said drug is administered at a dose of about 10 to about 1000 mg/day.

In the case of immunotherapy drugs such as cyclosporine, azathioprine, cyclophosphamide, said drug is administered at a dose of about 10 to about 1000 mg/day.

In another advantageous combined preparation of the invention, in the case of administration of a drug chosen among cytostatic compounds, apoptosis inducing compounds or cytokines, said drug is administered at a dose of about 0.1 to about 100 mg/day.

In the case of cytostatic compounds such as amoxifene, prodasone, sandostatine, polyamine inhibitors or apoptosis inducing compounds such as sodium butyrate or mitomycin C, said drug is administered at a dose of about 0.1 to about 100 mg/day.

In another advantageous combined preparation of the invention, the immunotherapy or chemotherapy drug is administered in a repeated way up to 10 times, the interval between each administration being between one day to two months.

In another advantageous combined preparation of the invention, the chemotherapy or immunotherapy drug and the monocyte derived cells are injected simultaneously.

In another advantageous combined preparation of the invention, the chemotherapy or immunotherapy drug and the monocyte derived cells are administered in sequential way, the immunotherapy or chemotherapy drug being administered before the monocyte derived cells.

In another advantageous combined preparation of the invention, the interval of time between the administration of the monocyte derived cells and the administration of the immunotherapy or chemotherapy drugs is of one day to two months.

In another advantageous combined preparation of the invention, the monocyte derived cells and the chemotherapy or immunotherapy drug are administered seqentially, the monocytes derived cells being administered before the immunotherapy or chemotherapy drug.

In another advantageous combined preparation of the invention, the interval of time between the administration of the immunotherapy or chemotherapy drug and the administration of the monocyte derived cells is of one day to two months.

In another advantageous combined preparation of the invention, the administration of monocyte derived cells is followed by an administration of chemotherapy or immunotherapy drug.

In another advantageous combined preparation of the invention, the interval of time between the administration of monocyte derived cells and the administration of chemotherapy or immunotherapy drugs is of one day to two months.

The invention also relates to a method for the treatment of residual cancer resistant to chemotherapy or of infectious diseases resistant to chemotherapy comprising the use of a combined preparation of the invention.

The invention also relates to a method for the treatment of infectious diseases resistant to antibiotic treatment comprising the use of a combined preparation of the invention.

BRIEF DESCRIPTION OF THE DRAWINGS

FIG. 1 corresponds to chemosensitive tumor and FIG. 2 corresponds to chemoresistant tumor.

DETAILED DESCRIPTION OF THE PREFERRED EMBODIMENT

Tumor cells have been grown for 3 days of cocultured at 37° C., 5% $CO_2$ from an initial seeding of $10^5$ cells under the following conditions presence of cisplatin, presence of human macrophages, presence of cisplatin and human macrophages.

The percentage of tumor cell survival is measured according to the method described in "Feasibility of drug screening with panels of human tumor cell lines using a microculture tetrazolium assay" (Alley M. C., Scudiero D. A., Monks A., et al.; Cancer Res., 1988, 48: 489–501), and is plotted against the dose of cisplatin (abscissa) in the test tube (molar concentration).

The amount of macrophages used in the experiment is constant.

Figure 1:
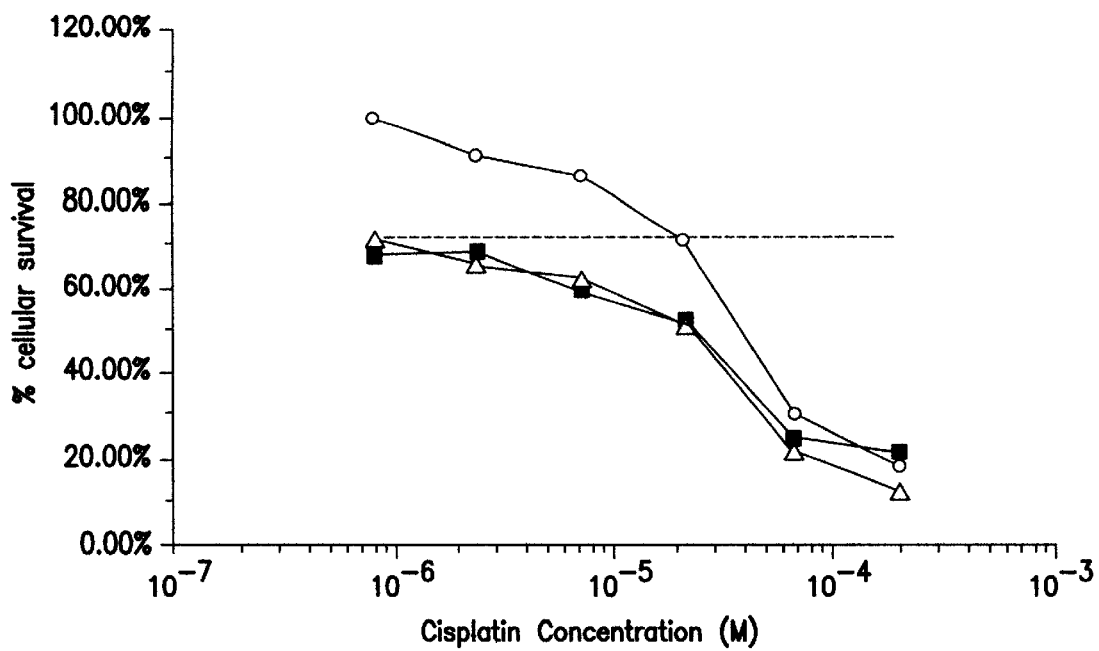
FIGS. 1 and 2 represent the in vitro synergy between chemotherapy (use of cisplatin) and macrophages (MAK) cytotoxicity on human ovary carcinoma tumor (IGR-OV1).
Figure 2:
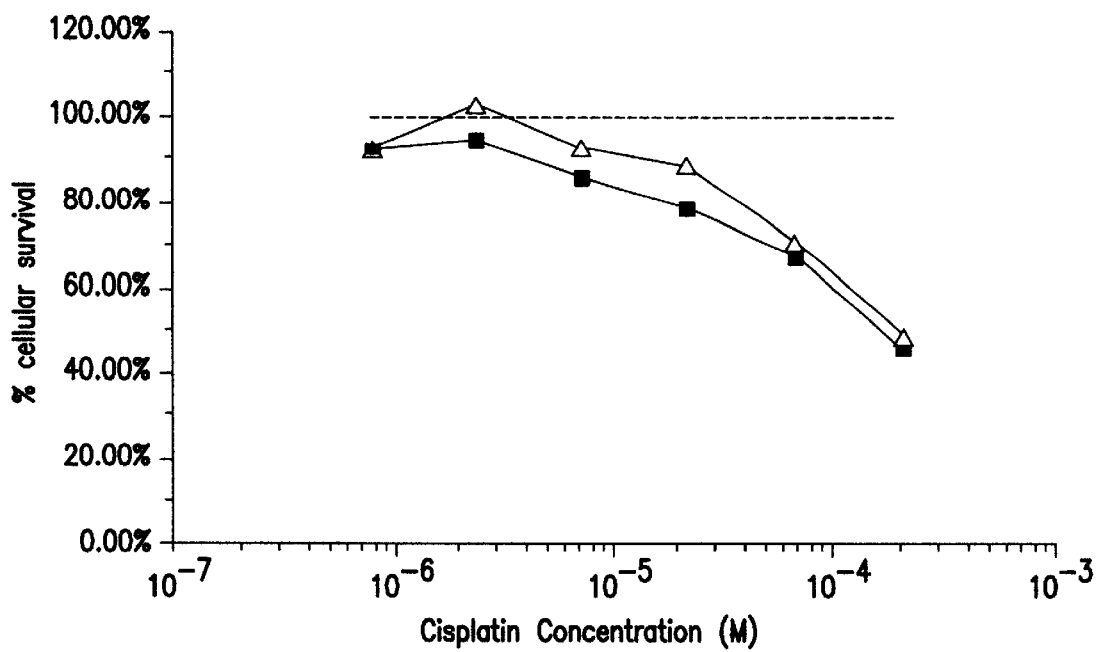

The initial ratio between macrophage and tumor cells is 4/1 for FIG. 1, and 1/1 in FIG. 2.

The dotted line corresponds to the addition of macrophages alone.

The open circle curve corresponds to the addition of cisplatin alone.

The dark square curve corresponds to the addition of macrophages and cisplatin.

The open triangle curve corresponds to the theoretical addition of the effects of macrophages alone, plus cisplatin alone.

On FIG. 2, the open circle curve and the open triangle curve are superimposed.

Additive effects of macrophages and cisplatin are seen on chemosensitive tumor cells. Synergy or potentiation of macrophages and cisplatin is observed for the chemoresistant tumor.

EXAMPLES

The following examples describe some applications of the invention

1) The synergy between macrophage immunotherapy and chemotherapy has been demonstrated in vitro on a carcinoma tumor cell line. Relative sensitivity of a human ovary tumor cell line and a derived line resistant to cisplatinum is documented, as well as the cytotoxicity of activated macrophages on these lines. Additive antitumoral effects for macrophages and cisplatinum is documented, allowing an effective dose response with lower levels of the drug, as demonstrated in FIG. 1 and FIG. 2.

2) Nude mice inoculated with human carcinoma solid tumors are, initially treated with cytotoxic drugs (Adriamycin, Etretinate, Taxotere), used alone or in combination. After a first response, the tumors grow again and the animals are treated systemically, or locally by injection of 1 million activated human macrophages which allow tumor stabilization. A second treatment with the same cytotoxic drugs used initially allow further antitumoral effect documented by measurement of subcutaneous tumor size.

3) Three patients with colorectal cancer and four patients with lung mesothelioma became resistant to 5-fluorouracil+ Cisplatin (or its oxaliplatin derivative) chemotherapy. They then have been injected with autologous activated macrophages and they have presented tumor stabilization or partial response illustrated by radiography. After a few months, the tumor relapsed and cancer evolution was reported. A second chemotherapy treatment, with similar cocktail of cytotoxic drugs, induced complete responses or major partial responses. This indicates a modification of the chemoresistance caused by immunotherapy.

4) Patients with prostate cancer treated by radio and chemotherapy present a 50% relapse rate of their cancer within 2 years. A treatment with activated macrophages is proposed after the conventional therapy. The time of relapse within 2 years as well as the evolution of the tumor are documented.

5) Bacterial infections induced in nude mice are relatively resistant to antibiotics. Effective therapy is achieved by sequential injection of macrophages and of antibiotics at usually ineffective doses. The additive effects of classical anti-infections drugs and of macrophage immunotherapy are documented.

6) Patients with myeloid leukemia, or with multiple myeloma, are treated with high dose chemotherapy. During the 6 weeks of aplasia, they present multiple infections, in particular nosocomial infections. Injections of activated macrophages during this period is performed to prevent infections and to allow a cure at lower doses of antibiotics.

7) C57B16 mice bearing solid carcinoma are injected intraperitonealy with a drug inducing apoptosis (1 mg mitomycin C or 0.1 mg sodium butyrate). After 24 h, mice are injected with 0.1 million monocyte derived cells in tumor periphery. Tumor regression and protection against further tumor challenge is observed only after this combined treatment. In another protocol, carcinoma cells are treated in vitro with 0.01 mM sodium butyrate, and then submitted to phagocytosis by murine monocyte derived cells. Injection of mice with 0.1 million of these monocyte derived cells protects the animals against carcinomachallenge.

In a particular embodiment of the invention, macrophages are loaded ex vivo with a drug as promyxin (a bioreductive agent) active in hypoxic areas. In this case, the macrophages having been fed with the drug, concentrate in the necrotic/ hypoxic area, kill tumor cells in contact and release locally during several days the cytotoxic drug killing the remaining cancer cells. A radiotherapy enhancer (tirazone) is also loaded into macrophages which cause, after reinjection, a potentiation of radiotherapy at specific tumor sites.

In another embodiment of the invention, an antibiotic is loaded into macrophages from patients with nosocomial infections resistant to conventional antibiotics.

The proper sequence and timing of macrophages injections, allowing maximum activity at the tumor or infectious site, are disclosed.

What is claimed is:

1. A combined preparation consisting essentially of as active substance the following individual components, in the form of a kit-of-parts:

cytotoxic macrophages, and at least one chemotherapy drug selected from the group consisting of anthracyclins, daunorubicin, adriamycin, taxoter derivatives, vinca alcaloids, vincristine, taxol, carmustine, cisplatin, fluorouracils, polyamine inhibitors, topoisomerase inhibitors, tamoxifene, prodasone, sandostatine, sodium butyrate, mitomycin C, penicilins, ꓱ-lactamines, caphalosporines, cyclines, aminoglucosidescosides, macrolides, sulfamides, AZT, protease inhibitors, acyclovir, retrovir and foscarnet;

wherein said cytotoxic macrophages are present in said kit-of-parts as a first injectable solution, and wherein said at least one chemotherapy drug is present in said kit-of-parts as a second injectable solution physically separate from said first injectable solution, said macrophages being suspended in said first injectable solution at a concentration yielding a dose of about $10^7$ to about $10^{10}$ monocyte derived cells per injection.

2. The combined preparation according to claim 1, wherein the cytotoxic macrophages contain chemotherapy drugs.

3. The combined preparation according to claim 1, wherein the cytotoxic macrophages are prepared according to a method comprising the following steps:

1) recovery of blood derived mononuclear cells directly from blood apheresis or from blood bag collection, followed by centrifugation, to eliminate a substantial part of red blood cells granulocytes and platelets, and collection of peripheral blood leukocytes;

2) washing peripheral blood leukocytes obtained at the preceding steps to obtain mononuclear cells;

3) resuspension of the total mononuclear cells (monocytes+lymphocytes) obtained at the preceding step in culture medium (RPMI or IMDM type) at $10^6$ to $2.10^7$ cells/ml, and culture for 5 to 10 days at 37° C. under $O_2/CO_2$ atmosphere in hydrophobic gas permeable bags, to obtain cytotoxic macrophages and contaminating lymphocytes.

4. The combined preparation according to claim 1, wherein the cytotoxic macrophages are administered at a dose of about $10^8$ to about $10^9$.

5. The combined preparation according to claim 1, wherein the cytotoxic macrophages are administered in a repeated way up to ten times, the interval between each administration being between three days to two months.

6. The combined preparation according to claim 1, wherein the chemotherapy drug is administered at a dose of about 0.1 to about 1000 mg/day.

7. The combined preparation according to claim 1, wherein the chemotherapy drug is administered in a repeated way up to 10 times, the interval between each administration being between one day to two months.

8. The combined preparation according to claim 1, wherein the chemotherapy drug and the cytotoxic macrophages are injected simultaneously.

9. The combined preparation according to claim 1, wherein the chemotherapy drug and the cytotoxic macrophages are administered in sequential way, the chemotherapy drug being administered before the cytotoxic macrophages.

10. The combined preparation according to claim 9, wherein the interval of time between the administration of the cytotoxic macrophages and the administration of the chemotherapy drugs is of one day to two months.

11. The combined preparation according to claim 1, wherein the cytotoxic macrophages and the chemotherapy drug are administered sequentially, the cytotoxic macrophages being administered before the chemotherapy drug.

12. The combined preparation according to claim 11, wherein the interval of time between the administration of the chemotherapy drug and the administration of the cytotoxic macrophages is of one day or two months.

13. The combined preparation according to claim 9, wherein the administration of cytotoxic macrophages is followed by an administration of chemotherapy drug.

14. The combined preparation according to claim 13, wherein the interval of time between the administration of cytotoxic macrophages and the administration of chemotherapy drugs is of one day or two months.

* * * * *